United States Patent [19]

Neubauer et al.

[11] Patent Number: 4,882,430

[45] Date of Patent: Nov. 21, 1989

[54] RECOVERY OF CAPROLACTAM FROM CAPROLACTAM DISTILLATION LOW BOILERS OR HIGH BOILERS OR MIXTURES THEREOF

[75] Inventors: Gerald Neubauer, Weinheim, Fed. Rep. of Germany; Emile De Decker, Schoten, Belgium; Hugo Fuchs, Ludwigshaften, Fed. Rep. of Germany; Bernhard Holzknecht, Ellerstadt, Fed. Rep. of Germany; Josef Ritz, Ludwigshafen, Fed. Rep. of Germany

[73] Assignee: BASF Aktiengesellschaft, Ludwigshafen, Fed. Rep. of Germany

[21] Appl. No.: 257,274

[22] Filed: Oct. 13, 1988

[51] Int. Cl.$^4$ .............................................. C07D 201/16
[52] U.S. Cl. .............................................. 540/540
[58] Field of Search ...................................... 540/540

[56] References Cited

U.S. PATENT DOCUMENTS 2,813,858  8/1954  Joris ..................................... 540/540

FOREIGN PATENT DOCUMENTS 0022161  11/1982  European Pat. Off. ............ 540/540

Primary Examiner—Robert T. Bond
Attorney, Agent, or Firm—Keil & Weinkauf

[57] ABSTRACT

Caprolactam is recovered from caprolactam distillation low boilers or high boilers or mixtures thereof by the following steps:
(a) crystallizing a low or high boiler or a mixture thereof to form purified capro-lactam crystals and a mother liquor,
(b) separating off the purified caprolactam crystals to leave a mother liquor,
(c) recycling from 5 to 90% by weight of the mother liquor of stage (b) into stage (a) and transferring the remainder of the mother liquor into the subsequent stage (d),
(d) crystallizing the remaining mother liquor portion from stage (c) to form caprolactam crystals and a mother liquor, separating off the caprolactam crystals of stage
(e) (d) and recycling the same into stage (a) to leave a mother liquor,
(f) recycling from 20 to 99% by weight of mother liquor of stage (e) into stage (d) and channeling out the remainder of the impurity-containing mother liquor of stage (e).

8 Claims, 1 Drawing Sheet

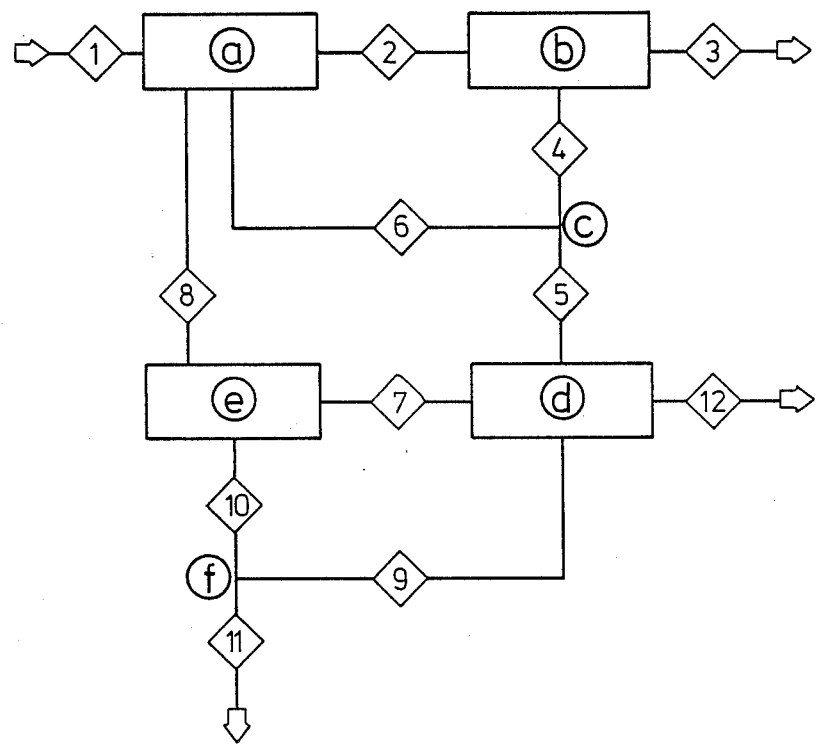

RECOVERY OF CAPROLACTAM FROM CAPROLACTAM DISTILLATION LOW BOILERS OR HIGH BOILERS OR MIXTURES THEREOF

In the course of its preparation and purification, caprolactam is separated by distillation from low-boiling and high-boiling products. Both the low-boiling and the high-boiling products still contain appreciable amounts of caprolactam. It is advisable to recover it from the distillation side streams and use it.

In a process described in EP Application No. 22,161, the alkaline distillation residue is distilled in a first stage under reduced pressure at a base of column temperature of from 130° to 160° C. to remove initially caprolactam, and the then remaining residue is distilled in a second stage under reduced pressure at a base of column temperature of from 140° to 180° C. to remove further caprolactam which is treated in a third stage with an acid and returned into the purification for the caprolactam from the Beckmann rearrangement. Such a process is technically complicated and is not sufficiently successful in eliminating difficult-to-remove compounds.

The obvious choice of removing byproducts from the low-boiling portions by distillation is not very effective, since it is very distillation-intensive and, what is more, the boiling points of the byproducts are very close to that of caprolactam.

U.S. Pat. No. 2,813,858 discloses purifying caprolactam by fractional crystallization, but no indication is given as to how to proceed with the purification of caprolactam distillation low or high boilers or mixtures thereof.

It is an object of the present invention to work up caprolactam distillation low or high boilers or mixtures thereof to recover the caprolactam contained therein and to do so while substantially reducing the levels of difficult-to-remove compounds in order that the caprolactam thus obtained may be used without disadvantages.

We have found that this object is achieved with a process for recovering caprolactam from a caprolactam distillation low boiler or high boiler or a mixture thereof, comprising the following steps:

(a) crystallizing a caprolactam distillation low or high boiler or a mixture thereof to form purified caprolactam crystals and a mother liquor, (b) separating off the purified caprolactam crystals to leave a mother liquor, (c) recycling from 5 to 90% by weight of the mother liquor of stage (b) into stage (a) and transferring the remainder of the mother liquor into the subsequent stage (d), (d) crystallizing the mother liquor portion from stage (c) to form caprolactam crystals and a mother liquor, (e) separating off the caprolactam crystals of stage (d) and recycling the same into stage (a) to leave a mother liquor, (f) recycling from 20 to 99% by weight of the mother liquor of stage (e) into stage (d) and channeling out the remainder of the impurity-containing mother liquor of stage (e).

The novel process has the advantage that it is possible to work up caprolactam distillation low boilers or high boilers individually or conjointly with the recovery of caprolactam in a simple manner. The conjoint workup has the advantage that no separate purifying operations are necessary. Furthermore, the novel process has the advantage that even difficult-to-remove impurities are substantially reduced in concentration. Moreover, the novel process has the advantage that the bulk of the caprolactam present in the low and high boilers is recovered in a simple manner in a usable form.

According to the invention, the starting materials are low boilers or high boilers or mixtures thereof obtained in the purification of caprolactam. Such distillation side streams are obtained for example in a multistage distillation where the low boilers are separated off overhead and, after pure caprolactam has been separated off, low boilers are obtained under reduced pressure at base of column temperatures of from 120° to 150° C. Suitable low boilers and high boilers are obtained for example by the process described in EP No. 22,161. Advantageously, the low boilers and high boilers are worked up conjointly in the form of a mixture. Advantageously, the mixture contains from 0.1 to 10 parts by weight of heavy boilers per part by weight of low boilers. The starting mixture thus obtained contains for example from 90 to 99.9% by weight of caprolactam and from 0.1 to 10% by weight of impurity. The impurity includes inter alia: different amounts of N-phenylacetamide, N-methylcaproamide, 6-methylvalerolactam, 7-methyllactam, 3-methyllactam and octahydrophenazine.

Caprolactam is isolated from the caprolactam distillation low boilers or high boilers or mixtures thereof by crystallization with depletion in the levels of impurities. Suitable for this purpose are prior art crystallization methods such as layer crystallization whereby caprolactam is deposited onto a cooled surface as a crystal layer and separated from the mother liquor residue. Also suitable are crystallization methods where the medium to be crystallized is agitated to produce a crystalline slurry comprising crystalline caprolactam and mother liquor and the caprolactam crystals are then separated off in a conventional manner for example by centrifuging. The latter method is particularly useful in the form of a vacuum crystallization as described for example in U.S. Pat. No. 2,813,858.

According to the invention, low boilers or high boilers or mixtures thereof are crystallized in stage (a) to form purified caprolactam crystals and a mother liquor. Advantageously, the crystallization is carried out to a degree of crystallization of from 20 to 60%, in particular of from 25 to 40%, the degree of crystallization being the weight percentage of crystalline caprolactam, based on the mixture used. The remainder is the liquid mother liquor. It has also proved advantageous to maintain during the crystallization in stage (a) a water content of from 5 to 20% by weight, in particular of from 10 to 15% by weight, based on the mixture used. Particularly advantageously, a vacuum crystallization is carried out under reduced pressure, for example of from 5 to 150 mbar, and at from 15° to 60° C.

The purified caprolactam crystals thus obtained and the mother liquor are separated in stage (b). If layer crystallization is employed, the mother liquor is discharged and the crystals obtained are melted separately. If crystals have been produced for example by mixing to give a slurry of caprolactam crystals and mother liquor, the slurry is preferably separated by centrifuging into caprolactam crystals and mother liquor. The purified caprolactam crystals thus obtained are advantageously recycled into the caprolactam synthesis, for example in the crude lactam extraction stage.

In stage (c), from 5 to 90% by weight of the mother liquor obtained in stage (b), for example from 10 to 80% by weight, are recycled into stage (a) for crystallization, together with fresh starting mixture. The remainder of the mother liquor of stage (b), amounting for example to from 10 to 95% by weight, is passed into the subsequent stage (d).

In the subsequent stage (d), the mother liquor from (c) is crystallized to form caprolactam crystals and a mother liquor. Advantageously, the degree of crystallization maintained here is from 20 to 60%. Advantageously, the crystallization is carried out under reduced pressure, for example at from 5 to 150 mbar, and at from 15° to 60° C. Furthermore, water is advantageously distilled off during the crystallization, for example from 10 to 50% by weight of the water present in the mother liquor used.

In stage (e), the crystals and the mother liquor from (d) are separated similarly to stage (b) into crystalline caprolactam and a mother liquor. The crystalline caprolactam thus obtained is again recycled into stage (a) and crystallized anew with fresh starting mixture and mother liquor from stage (c).

In stage (f), from 20 to 99% by weight of the impurity-containing mother liquor from stage (e), preferably from 30 to 98.5% by weight, are separated off and recycled back into stage (d) for crystallization, while the remainder of the mother liquor from stage (e) is channeled out to remove the impurities.

A particularly useful technique is a vacuum crystallization where in stage (a) low or high boilers or mixtures thereof are crystallized under from 5 to 150 mbar at from 15° to 60° C. with the water content maintained at from 5 to 20% by weight to form a slurry comprising from 20 to 60% by weight of purified caprolactam crystals and a mother liquor and in stage (b) the slurry obtained in (a) is separated, for example by centrifuging, into purified crystalline caprolactam, which is separated off and channeled out, and a mother liquor, which stays behind.

In stage (c), from 10 to 80% by weight of the mother liquor left in stage (b) are recycled into stage (a) and the remainder is passed into the subsequent stage (d).

In stage (d), the remainder of the mother liquor from stage (c) is crystallized under from 5 to 150 mbar at from 15° to 60° C. with removal by distillation of from 10 to 50% by weight of the water contained in the mother liquor, to form a slurry comprising from 25 to 55% by weight by crystalline caprolactam and a mother liquor.

In the subsequent stage (e), the crystalline caprolactam is separated from the slurry produced in stage (d) and recycled into stage (a), leaving a mother liquor.

(f) Of the mother liquor produced in stage (e), from 30 to 98.5% by weight are recycled into crystallization stage (d), and the remainder of the impurity-containing mother liquor is channeled out.

The process of the invention is illustrated by the following Example:

EXAMPLE

A mixture of first runnings (low boiler) and bottom product (high boiler) from a lactam distillation column in a ratio of 1:1.15 is added in accordance with FIG. 1 via 1 to the 1st crystallization stage (a) in an amount of 114.6 kg per hour and the following composition:

```
100  kg of lactam
1.8  kg of impurity (low and high boilers)
12.8 kg of water.
     Via line 6 a mixture of
71.4 kg of lactam
5.8  kg of impurity
9.4  kg of water
``` is added to the 1st crystallization stage from stage (e). Crystals from the 2nd crystallizer stage (d) are passed via line 8 into crystallizer 1 in the following composition:

```
99.5 kg of lactam
6.8  kg of impurity
1.3  kg of water.
```

In the 1st crystallization stage a crystallization is carried out at 35° C. and 20 mbar. The inlet temperature is about 40° C. The temperature is maintained by evaporative cooling. The crystallizer is stirred at 90 rpm.

The resulting slurry (30% by weight of crystals) passes via 2 into a pressure centrifuge (b) operating at 2000 rpm. The crystals obtained here in the composition

```
98   kg of lactam
0.4  kg of impurity
0.7  kg of water
``` are channeled out and returned back into the main stream of the lactam purification stage of the caprolactam synthesis.

The mother liquor obtained from the centrifuging step (b) is passed in an amount of (59% by weight of mother liquor)

```
101.5 kg of lactam
8.2   kg of impurity
13.4  kg of water
``` via line 5 into the 2nd crystallization stage (d).

Via line 6 the above-described mother liquor (41% by weight) is introduced into the 1st crystallization stage (a).

The slurry obtained in crystallization stage d is separated in a centrifuge (e), and the crystal portion is passed as described via line 8 into stage (a).

While the mother liquor is passed in an amount of

```
102.7 kg of lactam
71.5  kg of impurity
13.5  kg of water (98% by weight)
``` via line 9 into the 2nd crystallization stage (d),

```
2    kg of lactam
1.4  kg of impurity
0.3  kg of water
``` of the mother liquor are channeled out via line 11 and discarded.

To maintain the water concentration, 11.8 kg of water (9.6% by weight) are vaporized in stage (d) under the conditions of stage 1 and channeled out.

To characterize the starting material in comparison with the crystalline product, the parameters customary for lactam and the impurities difficult to remove by distillation are reported:

| Starting material | | Crystals |
|---|---|---|
| liquid bases meq/kg | 3.36 | 0.8 |
| GC impurity ppm | 552 | 130 |
| including inter alia | | |
| N—pentylacetamide | 160 | 40 |
| N—methylcaproamide | 47 | 10 |
| 6-methylvalerolactam | 78 | 18 |
| 7-methyllactam | 90 | 21 |
| 3-methyllactam | 38 | 8 |
| octahydrophenazine | 1.7 ppm | 0.3 |

COMPARATIVE EXAMPLE 1

If the distillative separation of low boilers is carried out in a column containing a bed of packing (Pall rings) 10 m deep under a top of column pressure of 10 mbar and a reflux ratio of 40, impurities having a boiling point close to that of lactam are not separated off completely:

| Feed for low boiler removal | | Distillation residue following low boiler removal |
|---|---|---|
| liquid bases meq/kg | 2.3 | 2.3 |
| GC impurity ppm | 1200 | 900 |
| including inter alia | | |
| N—pentylacetamide | 300 | 220 |
| N—methylcaproamide | 90 | 65 |
| 6-methylvalerolactam | 190 | 160 |
| 7-methyllactam | 220 | 190 |
| 3-methyllactam | 90 | 85 |
| octahydrophenazine | 0.5 | 0.5 |

While GC impurities were only slightly reduced in concentration in the course of the distillation, the impurities particularly difficult to separate off by distillation decreased by a factor of $\approx 4$ in the course of the crystallization.

COMPARATIVE EXAMPLE 2

On trying to separate the high boiler-containing lactam by distillation the amount of octahydrophenazine (which is particularly difficult to separate off) in the distillate remains virtually unchanged, the following result being obtained:

| | Feed | Distillate |
|---|---|---|
| GC impurity ppm | 220 | 200 |
| octahydrophenazine | 2.5 | 2.2 |

We claim:

1. A process for recovering caprolactam from a caprolactam distillation low boiler or high boiler or a mixture thereof, comprising the following steps:
   (a) crystallizing a low or high boiler or a mixture thereof to form purified capro-lactam crystals and a mother liquor,
   (b) separating off the purified caprolactam crystals to leave a mother liquor,
   (c) recycling from 5 to 90% by weight of the mother liquor of stage (b) into stage (a) and transferring the remainder of the mother liquor into the subsequent stage (d),
   (d) crystallizing the mother liquor portion from stage (c) to form caprolactam crystals and a mother liquor,
   (e) separating off the caprolactam crystals of stage (d) and recycling the same into stage (a) to leave a mother liquor,
   (f) recycling from 20 to 99% by weight of the mother liquor of stage (e) into stage (d) and channeling out the remainder of the impurity-containing mother liquor of stage (e).

2. A process as claimed in claim 1, wherein a degree of crystallization of from 20 to 60% is maintained in stages (a) and (d).

3. A process as claimed in claim 1, wherein in stage (c) from 10 to 80% by weight of the mother liquor is recycled into stage (a) and the remainder is passed into stage (d).

4. A process as claimed in claim 1, wherein in stage (f) from 30 to 98.5% by weight of the mother liquor is recycled into stage (d) and the remainder is channeled out.

5. A process as claimed in claim 1, wherein in stage (a) a water content of from 5 to 20% by weight is maintained.

6. A process as claimed in claim 1, wherein the crystallization in stages (a) and (d) is carried out under reduced pressure at from 15° to 60° C.

7. A process as claimed in claim 1, wherein the following steps are carried out:
   (a) crystallizing a low boiler or a high boiler or a mixture thereof under from 5 to 150 mbar at from 15° to 60° C. while maintaining a water content of from 5 to 20% by weight to form a slurry comprising from 20 to 60% by weight of purified caprolactam crystals and a mother liquor,
   (b) separating off the purified caprolactam crystals to leave a mother liquor,
   (c) recycling from 10 to 80% by weight of the mother liquor of stage (b) into stage (a) and transferring the remainder of the mother liquor into the subsequent stage (d),
   (d) crystallizing the remainder of the mother liquor from stage (c) under from 5 to 150 mbar at from 15° to 60° C. with distillative removal of from 10 to 50% by weight of the water contained in the mother liquor to form a slurry comprising from 25 to 55% by weight of crystalline caprolactam and the mother liquor,
   (e) separating the crystalline caprolactam from the slurry obtained in stage (d) and recycling the caprolactam crystals into stage (a), leaving behind a mother liquor, and
   (f) recycling from 30 to 98.5% by weight of the mother liquor of stage (e) into stage (d) and channeling out the remainder of the impurity-containing mother liquor.

8. A process as claimed in claim 1, wherein a mixture of caprolactam distillation low boilers and high boilers is used.

* * * * *

UNITED STATES PATENT AND TRADEMARK OFFICE
CERTIFICATE OF CORRECTION

PATENT NO. : 4,882,430

DATED : November 21, 1989

INVENTOR(S) : Gerald NEUBAUER, et al.

It is certified that error appears in the above-identified patent and that said Letters Patent is hereby corrected as shown below:

On the title page:

The benefit of foreign priority has been timely claimed and should read:
--FOREIGN APPLICATION PRIORITY DATA
Oct. 16, 1987 [DE] Fed. Rep. of Germany 3735054--

Signed and Sealed this

Second Day of July, 1991

Attest:

HARRY F. MANBECK, JR.

Attesting Officer

Commissioner of Patents and Trademarks